United States Patent von Bezold et al.

[11] 4,029,091
[45] June 14, 1977

[54] OSTEOSYNTHESIS

[76] Inventors: Götz-Dietrich von Bezold, 34 Ammerseestr., Gauting; Werner Kraus, 13 Bauerstr., Munich, both of Germany

[22] Filed: Aug. 11, 1975

[21] Appl. No.: 603,562

[30] Foreign Application Priority Data

Aug. 12, 1974 Germany .................. 2438669

[52] U.S. Cl. ................................ 128/92 D
[51] Int. Cl.² ................ A61B 17/18; A61F 5/04
[58] Field of Search ............ 128/92 D, 92 G, 92 R, 128/92 B, 82.1

[56] References Cited

UNITED STATES PATENTS 2,580,821   1/1952   Nicola ........................ 128/92 D
3,786,806   1/1974   Johnson et al. ............... 128/92 D

FOREIGN PATENTS OR APPLICATIONS 335,797   3/1959   Switzerland ................. 128/92 D

*Primary Examiner*—Ronald L. Frinks
*Attorney, Agent, or Firm*—Flynn & Frishauf

[57] ABSTRACT

An Osteosynthesis plate for application to a fractured bone across a fractured site thereof by screws applied to said bone through screw holes of said plate, wherein resilient means is provided between at least two screw holes spaced in a longitudinal dimension of said plate, to allow for a limited movement of the said holes in respect to each other under the action of externally generated forces, which may be magnetic, the freedom of movement being restricted essentially to a direction parallel to said longitudinal dimension.

8 Claims, 6 Drawing Figures

POWER SOURCE

OSTEOSYNTHESIS

The present invention relates to an osteosynthesis plate for application to fractured bones across the fracture site and may take the form of either a single, integral plate or plate means having a main body to which exchangeable sub-units are attached.

It is an object of the invention to provide an osteosynthesis plate which enhances the healing of the fracture by enabling the application of a controlled continuous and/or oscillating force urging the bone fragments against each other.

The osteosynthesis plate according to the invention provides for controlled movements of the bone fragments attached by bone screws to the plate, the freedom of movement being restricted essentially to a longitudinal direction of the plate which has an elongated shape. The movement may be caused by forces other than mechanical forces produced by loading the fractured bone, specifically by magnetic forces produced by a magnetic field generated by e.g. a suitably excited solenoid coil positioned around the limb comprising the fractured bone provided with the osteosynthesis plate according to the invention.

Further features, advantages and objects of the invention will become apparent from the following description of preferred embodiments of the invention.

In the accompanying drawing

FIG. 1 shows an osteosynthesis plate having a body 10 in form of an elongated plate member having a thickness which is relatively small in comparison to the longitudinal and transversal dimensions of the plate. The body 10 is provided with countersunk apertures or holes through which bone screws can be applied into the fragments of the broken bone to which the plate is applied.

Figure 1:
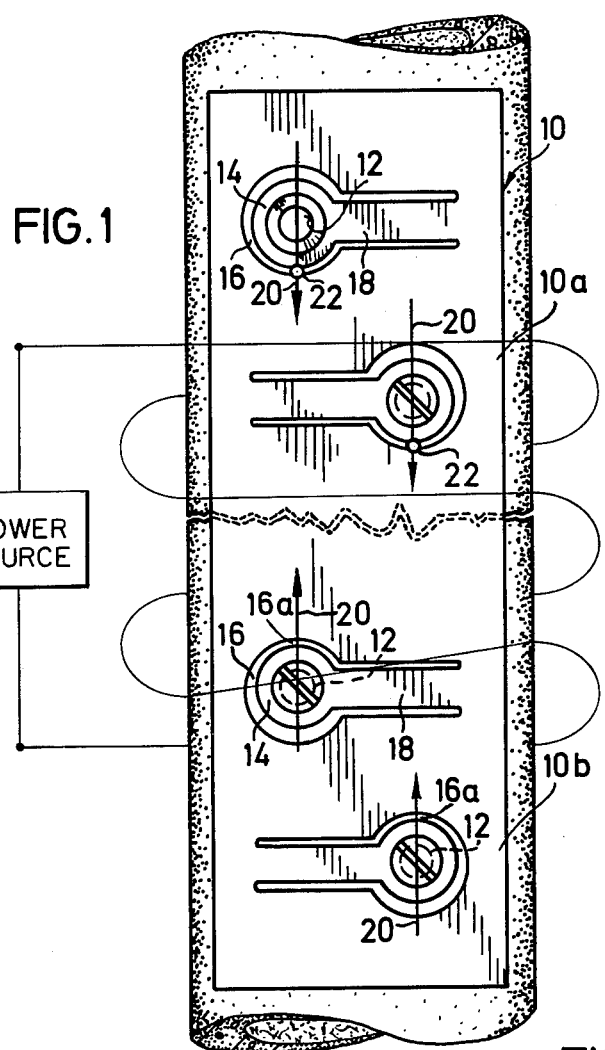
FIG. 1 is a somewhat simplified plan view of an osteosynthesis plate according to a first embodiment of the invention attached to a fractured bone.

At least one screw hole of the plate or a number of screw holes, or, as shown in FIG. 1, all of the screw holes are formed in lugs 14 which are separated by a gap 16 from the body 10 of the plate. Each lug is connected to the body 10 by a rod-like connection or cantilever element 18 which is separated from the body 10a by an extension of the gap 16. The cantilever element 18 has a width (measured in the longitudinal direction of the plate) such that it can act as resilient cantilever having a predetermined degree of stiffness and a resiliency.

Assumed that an upper portion 10a of the plate is attached to a first portion of a fractured cone, e.g. femur, and the other portion 10b of the plate is attached to a second portion of said bone, it will be obvious that both portions of the bone can resiliently move towards each other upon application of a longitudinal force acting in the direction of the arrows 20 via the bone screws on the lugs. Such force may be produced by an external mechanical force acting on the respective limb, e.g. by the normal loading of the limb, or, if the limb is a leg, by pressing the leg against the bottom end of the bed.

The force which can bring the ends of the fractured bone more closely together, as described above, may be produced by other than mechanical means if the plate according to another aspect of the invention comprises a magnetically susceptible material, as a ferromagnetic material as iron, nickel, ferromagnetic alloys and ferromagnetic ceramics.

If the selected ferromagnetic material is incompatible to human (or animal) tissue, it should be clad by a compatible material, e.g. a noble metal, a chromium cobalt alloy known under the trade name "Vitallium" or by a tissue-compatible polymeric material as polyethylene or a carbon-fluorine-polymer. Alternatively, the main portion of the plate is made of a compatible material and ferromagnetic bodies are embedded at suitable places so that they will not come into contact with the tissue. Thus, a ferromagnetic body in form of a ring (not shown) may be incorporated into a lug 14 to surround the hole 12, and an rectangular or arcuate ferromagnetic body may be embedded in the main portion of the plate adjacent to the lug on the other side of the gap 16.

By application of an externally generated magnetic field, the ferromagnetic bodies or portion will develop attraction forces which tend to narrow the gap on one side of the lug and, thus, altering the longitudinal distance between the lugs, and thus the bone screws and thus, in turn of the bone fragments.

The gap 16 may be asymmetric, as shown in FIG. 1 in that it is on the one side (in the direction of the longitudinal dimension of the plate and of the freedom of movability of the lugs in respect to the main portion of the plate) somewhat smaller than on the opposed side, as shown in FIG. 1. Preferably, the gaps are narrower on that sides of the lugs which are nearer to the middle of the plate, where normally the fracture gap lies. An externally generated magnetic field will casue magnetic attraction forces which tend to diminish the width of the narrower gaps because there a higher flux density will be produced than across the wider gaps. Periodic, oscillatory or pulse-like forces may be produced by magnetic fields having a correspondingly varying field strength.

The effect described above by which the front ends of the fractured bones are forced closer together can be produced also with gaps having equal width on both longitudinal sides of the lugs. In such case, an inhomogeneous magnetic field must be produced, specifically a magnetic field which has its greatest strength in the plane extending through the fracture gap and diminishing with increasing distance in longitudinal direction. A field of this type may be produced by an annular magnetic coil which is relatively short in respect to the longitudinal dimension of the plate. A coil of this type is positioned around the fracture gap and excited by a suitable direct current, pulse current or low frequency alternating current having a frequency which is preferably below 25 c/s, e.g. 10 c/s or even much lower.

To prevent abrupt displacements of the lugs relative to the main portion of the plate, elastic spacers 22 may be provided which may take the form of small cylindrical bodies of a elastic polymeric material received in appropriately formed recesses in opposed edges of the lug and the main body. Alternatively, or in addition, the cross sectional area of the magnetizable material may be restricted such that the resulting magnetic saturation limits the attraction forces.

Figure 2:
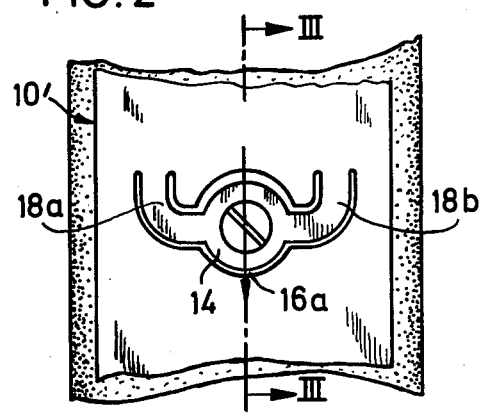
FIG. 2 is a plan view of a portion of an osteosynthesis plate according to a second embodiment of the invention.

FIG. 2 shows a portion of a plate 10' according to an embodiment of the invention which is modified in respect to the embodiment shown in FIG. 1. The embodiment shown in FIG. 2 comprises lugs 14 which are supported on opposite sides by intergral connecting members 18a and 18b. The connecting members 18a, 18b are curved to provide a spring-like elastic suspension and some freedom of movement of the respective lug 14 in the longitudinal direction. The connecting members have portions adjacent to the respective lug which extend essentially in transversal direction, and further portions between the said first portion and the main portion of the plate, which further portions extend essentially in the longitudinal direction. The lugs can be displaced in respect to the main portion of the plate 10a quite similar as described with reference to FIG. 1.

Figure 3:
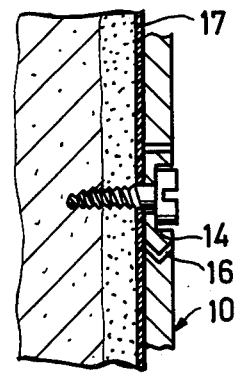
FIG. 3 is a cross sectional view in a plan labeled III-III in FIG. 2.

According to a further modification shown in FIG. 3, the lug 14 and the opposite portion of the plate 10 may be formed with a wedge-like projection and a mating slot, respectively, to enhance the stability of the plate and provide for some locking upon loading.

It is not necessary that all of the screw holes of the osteosynthesis plate are formed in movable lugs, as described with reference to FIG. 1 and 2. In fact, in most cases it is sufficient to provide only one longitudinal half of the plate with screw holes formed in resiliently displaceable lugs or similar members. This reduces the cost of manufacture and, however, the available range of displacement.

Figure 4:
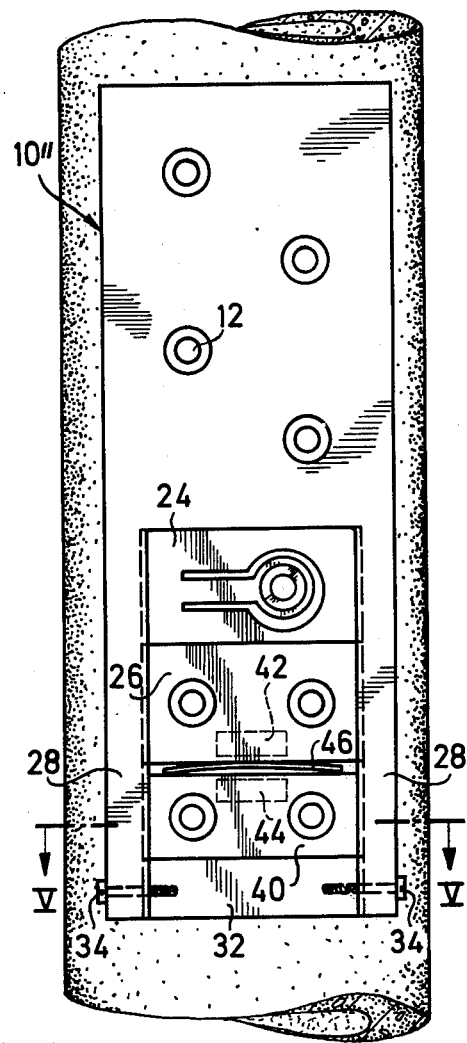
FIG. 4 is a plan view of an osteosynthesis plate showing further aspects of the invention.
Figure 5:
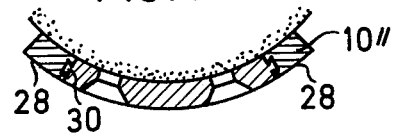
FIG. 5 is a cross sectional view in a plan labeled V-V in FIG. 4.

The embodiment shown in FIG. 4 and 5 comprises a plate 10" having a body, the upper portion of which is conventional and has screw holes 12, the position of which is fixed in respect to the body of the plate.

The lower portion comprises two lateral, rod-like extensions 28 integral with the upper portion and provided, at its opposed inner sides with dovetail keys for receiving insertable plate members of different types, e.g. one or several plate members 24 comprising resiliently supported lugs as described with reference to FIG. 1, or insert members 26 having fixed screw holes, and so on. In use, the space between the lateral extensions 28 will be completely filled with insert members and these are held in place by an end member 32 which in turn may be held in place by screws 34 extending through the extensions into the end member. The embodiment according to FIG. 4 allows to adapt the plate to a variety of different situations.

According to a further modification shown in the lower portion of FIG. 4, the dovetail key may receive an insertable plate member 40 which may be provided with fixed screw holes and which is urged by resilient means, e.g. a leaf spring 46 away from the adjacent plate member 26 (or an adjacent portion of the main body of the plate 10"). Further, a body of ferromagnetic material 44 may be incorporated into plate member 40, and a corresponding body 42 may be incorporated in the adjacent plate member (or near an adjacent margin of the main portion of the plate 10"). An externally produced magnetic field magnetizing the ferromagnetic bodies 42 and 44 will produce attraction forces which tend to bring the plate members 26 and 40 closer together against the action of the leaf spring 26.

Thus, a force urging the bone fragments attached to plate members 26 and 40 together may be externally produced. As a modification, the bodies 42, 44 can be made of a permanent magnetic material so that a permanent bias force is produced which urges the bone fragments together. In such case, a spacer (not shown) is provided between plate members 26 and 40 providing their maximum distance during the application of the plate to the fractured bone by the surgeon, said spacer being removed by the surgeon after application of the plate so that the attraction force provided by the permanent magnetic bodies can act on the bone fragments. This permanent magnetic attraction force may be altered, e.g. periodically, by an opposing external magnetic field. If an alteration of the force is desired, the permanent magnetic bodies are preferably magnetized only partially.

Figure 6:
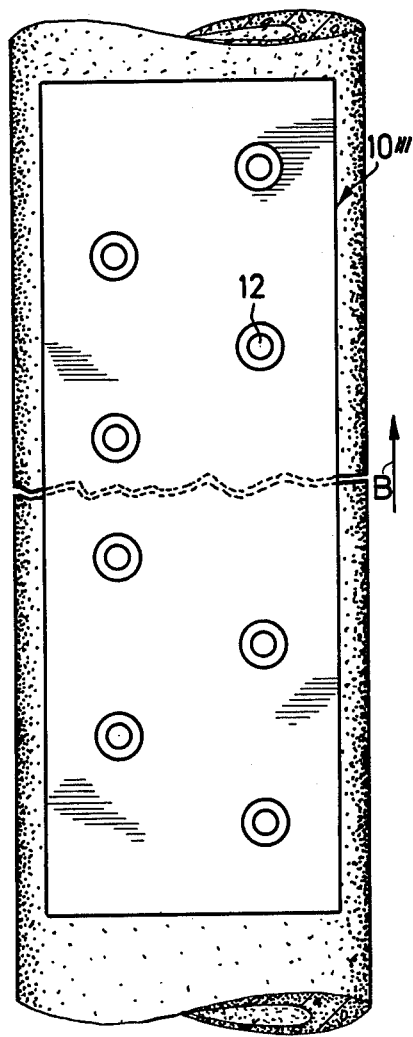
FIG. 6 is a plan view of an embodiment of the invention operating on the principle of magnetostriction.

The embodiment shown in FIG. 6 can take the form of a plate 10''' which is shaped in conventional manner. However, according to the invention, the plate 10''' consists of or comprises an magnetostrictive material, so that the longitudinal dimension of the plate, and thus, the mutual longitudinal distance of the screw holes 12 can be changed by an externally generated magnetic field B. The plate 10" may consists of or comprise e.g. nickel, barium titanate ceramic, or any other suitable material of high magnetic permeability and sufficient mechanical strength and exhibiting a magnetostrictive effect of sufficient magnitude.

The magnetic field used in connection with the embodiment shown in FIG. 6, and the previously described embodiments, may have field strength up to e.g. 1000 to 2000 Gauss and more.

It will be appreciated that various alterations and modifications of the described embodiments, and combinations of the features of different disclosed embodiments may be made without departing from the scope of this invention. While a leaf spring 46 is shown in FIG. 4 to urge the plate member 40 away from the adjacent member, other resilient or elastic means, e.g. hydraulic or pneumatic means may be provided instead. No individual magnetic bodies 42, 44 are necessary, if the plate members 26 and 40 are at least partially made of magnetizable or ferromagnetic or permanent magnetic material.

The magnetic bodies 42, 44 may take the form of annular members surrounding the bone screws (not shown in FIG. 4). A similar effect will be obtained by using a ferromagnetic or permanent magnetic material in or for the bone screws.

As shown in FIG. 3, a thin film or coating of a tissue-compatible material, e.g. a polymeric film, may be provided between the plate and the bone to which it is attached. This may reduce the frictional resistance between the bone and those portions of the plate which can move in respect to the bone. The coating or film 17 may be made e.g. of polyethylene or polytetrafluorethylene.

What is claimed is:

1. An osteosynthesis plate for application across a fractured site of a fractured bone, said plate having longitudinal and transverse dimension
    wherein said plate is formed with a plurality of openings therein having a major dimension extending in the direction of said transverse dimension;
    a plurality of lugs are provided, each formed with at least one resilient cantilever portion, said lugs being located in said openings, the cantilever portion being connected to the plate and resiliently supporting the lugs in position in said openings, said cantilever portions forming resilient spring and suspension means elastically supporting said lug for elastic movement in a direction which is limited essentially to a direction parallel to said longitudinal dimension.

2. The osteosynthesis plate as claimed in claim 1, wherein each lug is supported by at least one cantilever portion which extends essentially in the direction of said transverse dimension from said lug to a lateral portion of said plate.

3. The osteosynthesis plate as claimed in claim 1, wherein each lug is supported by two cantilever portions each having a first portion adjacent said lug and extending in the direction of said transverse dimension, and a second portion connecting said first portion to a main portion of said plate and extending essentially in the direction of said longitudinal dimension.

4. The osteosynthesis plate as claimed in claim 1, wherein each lug and cantilever portion supporting said lug within the respective opening of the plate is separated by a gap from an adjacent portion of said plate, said gap having portions of different width on longitudinally opposed sides of said lug and cantilever portion, and
  wherein said plate, and said lug and cantilever portion comprises a ferromagnetic material magnetizable by a magnetic field to produce attraction forces of different magnitudes across said gap portions of different width.

5. The osteosynthesis plate according to claim 4, wherein the gap portion of smaller width comprises means for restricting movements of said lug and cantilever portion which tends to reduce the width of said smaller gap portion.

6. The osteosynthesis plate as claimed in claim 1, wherein at least one lug within the respective opening of the plate is separated from an adjacent portion of the plate by a gap, and the adjacent portion of said plate and said lug comprise a material selected from the group of ferromagnetic or permanenet magnetic materials.

7. An osteosynthesis plate for application across a fractured site of a fractured bone, said plate having at least two screw holes spaced in a longitudinal direction of said plate wherein resilient means including magnetic materials is provided between said screw holes allowing a mutual displacement of said screw holes upon application of a magnetic field, said movement being restricted essentially to said longitudinal direction;
  and means generating a magnetic field and located to act on said magnetic materials.

8. An osteosynthesis plate for bone fractures having an elongated plate of magnetostrictive material formed with longitudinally spaced - with respect to the major direction of the bone - holes for receiving bone screws, wherein the distance of at least two screw holes (12) is changeable by the effect of an externally applied magnetic field;
  and means applying a magnetic field to said plate.

* * * * *

UNITED STATES PATENT AND TRADEMARK OFFICE
CERTIFICATE OF CORRECTION

PATENT NO. : 4,029,091
DATED : June 14, 1977
INVENTOR(S) : v.Bezold et al

It is certified that error appears in the above-identified patent and that said Letters Patent are hereby corrected as shown below:

Title should read "OSTEOSYNTHESIS PLATE" not "OSTEOSYNTHESIS"

Signed and Sealed this

Thirteenth Day of September 1977

[SEAL]

Attest:

RUTH C. MASON
*Attesting Officer*

LUTRELLE F. PARKER
*Acting Commissioner of Patents and Trademarks*